(12) United States Patent
Leschinski et al.

(10) Patent No.: US 8,686,182 B2
(45) Date of Patent: Apr. 1, 2014

(54) PROCESS FOR PREPARING ISOCYANATES AND/OR POLYISOCYANATES

(71) Applicant: BASF SE, Ludwigshafen (DE)

(72) Inventors: Julia Leschinski, Ixelles (BE); Torsten Mattke, Freinsheim (DE); Gerrit Waters, Karlsruhe (DE); Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/661,652

(22) Filed: Oct. 26, 2012

(65) Prior Publication Data

US 2013/0109883 A1 May 2, 2013

Related U.S. Application Data

(60) Provisional application No. 61/551,937, filed on Oct. 27, 2011.

(51) Int. Cl.
 *C07C 263/00* (2006.01)

(52) U.S. Cl.
 USPC ........................................................ 560/347

(58) Field of Classification Search
 None
 See application file for complete search history.

(56) References Cited

U.S. PATENT DOCUMENTS

| | | | |
|---|---|---|---|
| 2009/0281350 A1* | 11/2009 | Knoesche et al. | 560/347 |
| 2011/0213177 A1 | 9/2011 | Mattke et al. | |
| 2011/0230676 A1 | 9/2011 | Lehr et al. | |
| 2012/0095255 A1 | 4/2012 | Mattke et al. | |
| 2012/0226073 A1 | 9/2012 | Heinen et al. | |
| 2012/0251435 A1 | 10/2012 | Lehr et al. | |
| 2012/0253063 A1 | 10/2012 | Mattke et al. | |
| 2013/0006013 A1 | 1/2013 | Mattke et al. | |
| 2013/0043611 A1* | 2/2013 | Sachweh et al. | 264/4.7 |

FOREIGN PATENT DOCUMENTS

| | | |
|---|---|---|
| CN | 101104595 A | 1/2008 |
| GB | 761590 | 11/1956 |
| WO | WO 2008/006775 A1 | 1/2008 |

OTHER PUBLICATIONS

Abstract, CN 101104595, Jan. 16, 2008, Derwent World Patents Index®, Thomson Reuters (Professional) UK Ltd.*
U.S. Appl. No. 13/587,378, filed Aug. 16, 2012, Mattke, et al.
U.S. Appl. No. 13/687,670, filed Nov. 28, 2012, Mattke, et al.
International Search Report and Written Opinion of the International Searching Authority issued Feb. 13, 2013, in PCT/EP2012/071251 (with English Translation of Category of Cited Documents).

* cited by examiner

*Primary Examiner* — Karl J Puttlitz
(74) *Attorney, Agent, or Firm* — Oblon, Spivak, McClelland, Maier & Neustadt, L.L.P.

(57) ABSTRACT

The invention relates to a process for preparing isocyanates and/or polyisocyanates by reacting the corresponding amines with phosgene, optionally in the presence of an inert medium, in a reactor (1), a first reactant stream comprising the amine being supplied to the reactor (1) in liquid form, and a second reactant stream comprising the phosgene being supplied to the reactor in gaseous form. The reactor is a centrifugal reactor (1) having a packing (9) which rotates about a central axis (7) in a housing (13), the first reactant stream and the second reactant stream being supplied to the rotating packing (9) such that the reactant streams are mixed due to the centrifugal force in the rotating packing (9) and are transported outward, the mixing in the rotating packing (9) resulting in reaction of the phosgene with the amine to give the corresponding isocyanate or polyisocyanate.

20 Claims, 1 Drawing Sheet

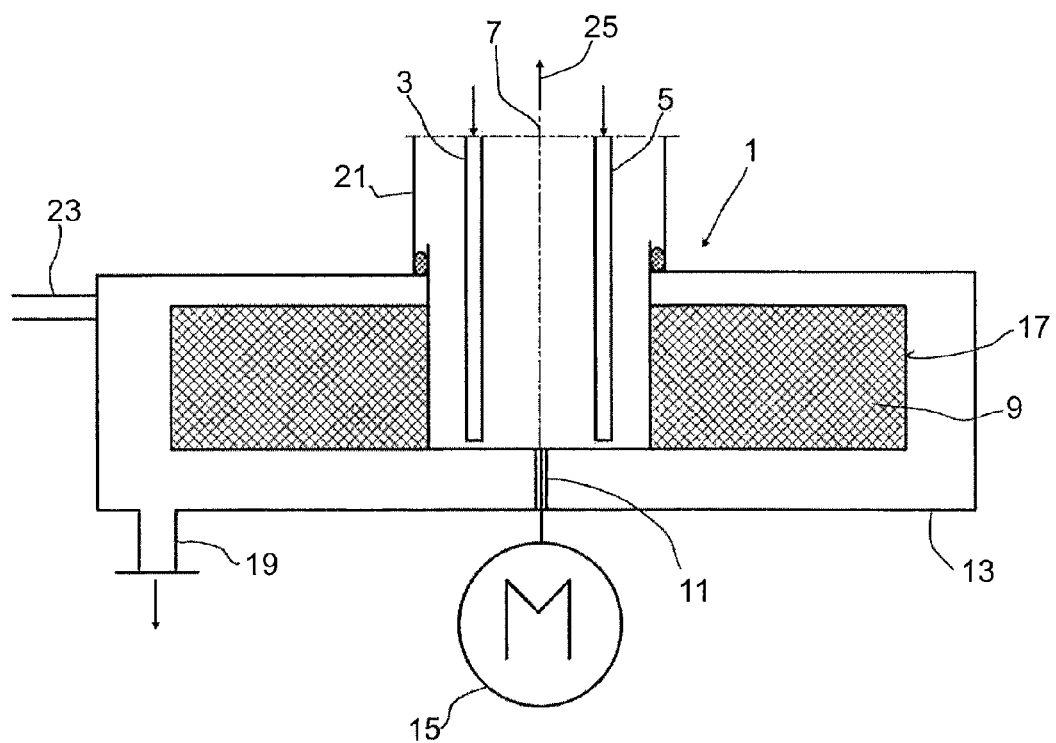

PROCESS FOR PREPARING ISOCYANATES AND/OR POLYISOCYANATES

The invention relates to a process for preparing isocyanates and/or polyisocyanates by reacting the corresponding amines with phosgene, optionally in the presence of an inert medium, in a reactor, a first reactant stream comprising the amine being supplied to the reactor in liquid form, and a second reactant stream comprising the phosgene being supplied to the reactor in gaseous form.

The preparation of isocyanates by phosgenation of the corresponding amines can in principle be effected by a liquid phase phosgenation or a gas phase phosgenation. Gas phase phosgenation is notable in that a higher selectivity, a lower holdup of toxic phosgene and a reduced energy demand are required. Compared to this, a liquid phase phosgenation is notable in that the reaction can be performed at lower temperatures, and vaporization of the reactants is not required.

In conventional liquid phase phosgenations, an amine-containing reactant stream is supplied in the liquid phase. This is mixed with a phosgene-containing reactant stream. The phosgene here may be dissolved in an inert solvent. Subsequently, the phosgene-containing reactant stream is sprayed into a mixing chamber in which it is mixed with the amine-containing reactant stream. The amine and the phosgene react with release of hydrogen chloride to form the corresponding isocyanates.

Since the isocyanate formed, in the case of an excessively low phosgene concentration, reacts with the excess amine to give urea or other troublesome, high-viscosity and solid by-products, rapid mixing of the amine with the phosgene is necessary.

In order to combine the advantages of liquid phase phosgenation with those of gas phase phosgenation, WO-A 2008/006775 discloses reacting the amines in the form of an aerosol with the phosgene. In order to ensure a high penetration rate of the phosgene into the liquid amine-containing phase, the droplets should be kept as small as possible. Droplet sizes of the amine are in the range from 10 nm to 1 mm. However, it should additionally be ensured here that the droplets are kept at such a size that an aerosol produced in the reaction can be deposited by downstream droplet/dust separators. The droplets and hence the aerosol can be produced, for example, by nozzles. A particular disadvantage of the process described here is the production of the aerosol and the subsequent removal of the droplets from the gas stream.

However, complete gas phase phosgenation may be undesirable, especially in cases in which the amine is decomposed in the course of heating. This is the case, for example, when the starting substances used are polyamines for preparation of polyisocyanates. These cannot be vaporized under the reaction conditions of the gas phase phosgenation.

For performance of a liquid phase phosgenation in which a liquid amine-containing stream and a liquid phosgene-containing stream react with one another, CN 101104595 A describes a centrifugal reactor. In this reactor, the liquid reactant streams are mixed and reacted rapidly. A disadvantage of the liquid phase phosgenation described here is, however, that the yield is low and relatively high energy consumption is necessary. In addition, a relatively high holdup of phosgene is required.

It is an object of the present invention to provide a process for preparing isocyanates and/or polyisocyanates, which does not have the disadvantages known from the prior art.

The object is achieved by a process for preparing isocyanates and/or polyisocyanates by reacting the corresponding amines with phosgene, optionally in the presence of an inert medium, in a reactor, a first reactant stream comprising the amine being supplied to the reactor in liquid form, and a second reactant stream comprising the phosgene being supplied to the reactor in gaseous form, wherein the reactor is a centrifugal reactor having a packing which rotates about a central axis in a housing, the first reactant stream and the second reactant stream being supplied to the rotating packing such that the reactant streams are mixed due to the centrifugal force in the packing and are transported outward, the mixing in the packing resulting in reaction of the phosgene with the amine to give the corresponding isocyanate or polyisocyanate.

First of all, the process according to the invention combines the advantages of gas phase phosgenation and of liquid phase phosgenation. The supply of the amine in the liquid phase allows the reaction to be performed at lower temperatures than a gas phase phosgenation. This also makes it possible to phosgenate amines which are not amenable to gas phase phosgenation. In addition, the process according to the invention can reduce the formation of by-products.

The use of the centrifugal reactor additionally has the advantage that there is no need to form aerosol droplets which have to be removed again from the gas stream after performance of the reaction. This also avoids the disadvantages of the known gas/liquid phosgenation, as described, for example, in WO-A 2008/006775.

In a centrifugal reactor, the gas phase is separated from the liquid phase at the exit from the rotating packing due to centrifugal force.

In the centrifugal reactor, very thin liquid films form on the rotating packing, which bring about high mass transfer between the gas phase and the liquid phase and are therefore positive for the reactive conversion of the amines.

A further advantage of the process according to the invention is that very short residence times can be achieved with the centrifugal reactor, which leads to minimal yield losses and high product qualities. A high product quality is understood in this context to mean a product with good color number, low chlorine content, high NCO numbers, an optimal molecular weight distribution, etc.

The reaction is performed preferably at a pressure in the range from 1 to 20 bar (absolute), more preferably in the range from 1 to 10 bar (absolute) and especially preferably in the range from 1 to 5 bar (absolute). The temperature is preferably in the range from 50 to 400° C., more preferably in the range from 100 to 300° C. and especially preferably in the range from 150 to 250° C.

In order to achieve a sufficiently low film thickness in the rotating packing of the centrifugal reactor, the centrifugal reactor is preferably operated in such a way that a centrifugal acceleration of 1 to 5000 g, more preferably a centrifugal acceleration in the range from 10 to 1000 g and especially preferably a centrifugal acceleration in the range from 50 to 250 g acts within the contact region of packing and liquid phase, where g is the acceleration due to gravity with a value of 9.81 m/s$^2$.

In order to avoid the formation of by-products in the reaction, it is advantageous to add the phosgene in excess. The addition of the phosgene in excess prevents the amine from reacting with hydrogen chloride to form a solid. The solid which forms in the reaction of the amine with hydrogen chloride can be phosgenated, but high reaction times are necessary for this purpose, which leads to yield losses in the phosgenation since the residence time of the solids is too high.

Phosgene unconverted in the reaction can—optionally after purification—be recycled and used for phosgenation.

Hydrogen chloride formed in the reaction can likewise, optionally after purification, be used to prepare vinyl chloride or to prepare hydrochloric acid. Alternatively, it is also possible to react the hydrogen chloride with oxygen by the Deacon process to give chlorine, and to recycle the latter into the phosgene synthesis.

The amines used, which are reacted by the process according to the invention for preparation of isocyanates, may be all customary amines. These are, for example, aliphatic diamines such as hexamethylenediamine (HDA), isophoronediamine (IPDA), and also tolylenediamine (TDA) and methylenedi(phenyldiamine) (MDA) in a mixture with higher homologs thereof. Especially in the case of phosgenation of MDA, the process according to the invention can be used particularly advantageously. Particular preference is given here to using 4,4'-MDA. This is generally present in a mixture with its isomeric compounds 2,2'-MDA and 2,4'-MDA. As well as the use of monomeric MDA, it is also possible to convert polymethylenedi(phenyldiamine) (PMDA) to the corresponding isocyanate by the process according to the invention. Since the boiling temperature of MDA is more than 300° C. and PMDA cannot be vaporized, the process according to the invention is particularly suitable for phosgenation of these amines to prepare the corresponding isocyanates.

In one embodiment of the invention, the first reactant stream comprising the amine additionally comprises at least one solvent. Solvents which are used here behave inertly before, during and after the reaction of the amines with the phosgene. Suitable solvents are, for example, organic solvents, for example aromatic solvents which may also be halogenated. Suitable solvents are, for example, toluene, monochlorobenzene, o- or p-dichlorobenzene, trichlorobenzene, chlorotoluene, chloroxylene, chloroethylbenzene, chloronaphthalene, chlorodiphenyl, xylene, decahydronaphthalene, benzene and mixtures thereof. Further suitable organic solvents are, for example, methylene chloride, perchloroethylene, hexane, diethyl isophthalate, tetrahydrofuran (THF), dioxane, trichlorofluoromethane, butyl acetate and dimethylformamide (DMF).

The use of the solvents can reduce the viscosity of the liquid first reactant stream comprising the amine, and thus give a lower film thickness. This allows faster mixing of the liquid reactant stream comprising the amine with the phosgene. In addition, given the same rotational speed, the liquid flows through the reactor at a higher speed, as a result of which the residence time can be reduced further.

The phosgene is preferably metered in in excess, based on the amine groups. The molar ratio of phosgene to amine groups is preferably 1.01:1 to 6:1, more preferably 1.1:1 to 4:1 and especially preferably 1.2:1 to 3:1.

A centrifugal reactor used in accordance with the invention to perform the process typically has a first feed for the first reactant stream and a second feed for the second reactant stream, in which case both the first reactant stream via the first feed and the second reactant stream via the second feed are supplied centrally to the packing. The central supply achieves the effect that the entire radial extent of the packing can be utilized for mixing of liquid reactant stream and gaseous reactant stream, and hence for performance of the reaction. In addition, the central supply achieves the effect that the liquid in the packing is accelerated to the maximum degree.

The first reactant stream and the second reactant stream can be supplied via two separate feeds, which are configured, for example, in the form of pipelines. Alternatively, it is also possible, for example, to use two concentric tubes, in which case the liquid first reactant stream is supplied through the inner tube and the gaseous second reactant stream through the outer tube. Alternatively, it is of course also possible that the gaseous second reactant stream is supplied through the inner tube and the liquid first reactant stream the outer tube.

The advantage of a concentric pipeline for supply of the reactant streams is that this supplies the reactant streams to the packing in homogeneous distribution over the circumference, and thus achieves homogeneous loading of the rotating packing.

The packing has channels through which liquid and gas can flow. Due to the rotation of the packing, a liquid film forms on the walls of the channels formed in the packing.

To form the channels, the packing of the centrifugal reactor may be of structured or unstructured design. In the packing, the liquid phase is mixed with the gaseous phase. The gas phase is preferably continuous. In the packing, a film flow forms, liquid flowing as a film on the surfaces of the packing, and the gas flowing through the empty volumes of the channels. At the exit from the packing, i.e. at the outer extent of the packing, a droplet flow arises, in which the liquid leaves the packing in the form of droplets. The droplets move within the gas phase which likewise emerges from the reactor.

It is preferable when the channels in the packing are configured such that the packing is porous and has a specific surface area of more than 200 $m^2/m^3$. This achieves a large surface area on which the liquid can form as a film, and thus enables a high throughput. More particularly, a porous packing permits more homogeneous wetting of the surfaces and hence a more homogeneous reaction.

Suitable materials for the packing are, for example, metals or ceramics. These are sufficiently resistant to the temperatures which occur in the reaction.

The rotating packing of the centrifugal reactor may be formed, for example, from unordered fibers or from a bed of spheres. However, other possible packings are those in the form of beds of random packing. The random packings used may be any other random packings. Examples of suitable random packings are cylinders, rings or Berl saddles. As well as the use of random packings, the rotating packing may also be in the form of structured internals, for example in the form of static mixers or monoliths or in any other form. A further option is the use of open-pore foams.

The rotating packing is accommodated in a fixed housing. The droplets which leave the packing are thrown outward due to the centrifugal force and hit the housing. A liquid film forms here on the wall of the housing, and flows downward due to gravity. The liquid is collected here and can be withdrawn from the housing via a liquid outlet.

Alternatively, it is also possible to additionally surround the packing with a ring, in which case the droplets leaving the packing hit the ring and drip off from the ring onto the housing base.

In this case too, the liquid is collected on the housing base and discharged via a liquid outlet. The gas is preferably withdrawn from the housing at the top side of the housing. This already achieves separation into gas and liquid in the reactor.

In a preferred embodiment, the reactor additionally has an inert gas inlet. An inert gas can be supplied to the reactor through the inert gas inlet. This allows the reactor to be purged, for example, with an inert gas before the reactor is put into operation. The inert gas here is likewise preferably withdrawn via the gas outlet through which the gaseous unreactive phosgene and the hydrogen chloride produced in the reaction are drawn off during the course of operation.

The liquid product stream which is withdrawn from the reactor typically comprises the isocyanate prepared, any solvent used and small amounts of by-products. The by-products which remain in the isocyanate can be separated from the isocyanate, for example, by an additional rectification or crystallization in a step following the reaction.

A working example of the invention is shown in the FIGURE and is explained in detail in the description which follows.

The sole FIGURE shows a schematic diagram of a centrifugal reactor used for preparation of isocyanates.

A first amine-comprising reactant stream is supplied via a first feed 3 to a centrifugal reactor 1. A second phosgene-containing gaseous reactant stream is supplied via a second feed 5. The first feed 3 and the second feed 5 are arranged such that they open into a packing 9 which rotates about a central axis 7. From the first feed 3 and the second feed 5, the reactant streams pass into the rotating packing 9. In the rotating packing 9 are formed channels on whose walls the first liquid reactant stream is deposited due to the rotation of the rotating packing 9 and the associated centrifugal force. On the walls of the rotating packing 9, a thin liquid film forms in this way and comes into contact with the phosgene of the second reactant stream. The phosgene reacts with the amine in the liquid to form isocyanate.

The rotating packing 9 may be configured as a structured or unstructured packing. For this purpose, it is possible, for example, to configure the rotating packing 9 in the form of a cage filled with filler material, for example random packings. Alternatively, it is also possible to manufacture the packing, for example, from fibers or spheres, it being preferable in the case of manufacture from spheres to sinter them to give a compact packing, in which case the channels are formed between the individual spheres.

It is especially preferable to configure the rotating packing 9 as a porous packing with a specific surface area of more than 200 $m^2/m^3$. This large specific surface area leads to a correspondingly good liquid distribution within the rotating packing 9 and hence to a low film thickness of the liquid on the walls of the packing. The low film thickness further improves mass transfer with the gaseous second reactant stream.

In order to drive the rotating packing 9, it is connected to a motor 15 via a shaft 11 through a housing 13. In order to obtain the desired rotational speeds, it is additionally possible that the motor 15 has a downstream gearbox.

The rotational speed of the rotating packing 9 is preferably in the range from 50 to 10 000 $min^{-1}$.

Due to the high rotational speed of the rotating packing and the resulting centrifugal forces, the liquid reactant stream is accelerated through the rotating packing 9 to the outer periphery. At the outer periphery 17 of the rotating packing 9, liquid droplets form and break off. The liquid droplets hit the wall of the housing 13 and run down to the base of the housing 13. At the base of the housing 13 is an outlet 19, through which the liquid reaction mixture is drawn off. Unreacted gaseous constituents, for example phosgene supplied in excess, and gaseous reaction products such as hydrogen chloride are preferably withdrawn from the centrifugal reactor 1 via a central gas outlet 21.

In order to be able to purge the centrifugal reactor 1 with an inert gas, especially before startup and alternatively also during operation, the housing also has a gas inlet 23.

In an alternative embodiment, it is also possible to surround the rotating packing 9 with a ring within the housing 13, in which case the ring is configured as an impact ring which is hit by the droplets which break off from the rotating packing 9. The droplets are deflected at the impact ring and directed to the base of the housing 13, such that the liquid can be withdrawn from the centrifugal reactor 1 via the liquid outlet 19.

The maximum rotational speed of the packing is preferably selected such that the droplets which break off have a size which allows simple removal by impact on the housing wall or the ring.

The liquid withdrawn via the outlet 19 can be worked up in a downstream step. More particularly, liquid or solid reaction by-products can be removed from the desired reaction product, namely the isocyanate.

The gas withdrawn via the gas outlet 21, which is shown here by an arrow 25, can likewise be processed. More particularly, it is preferable to separate the offgas 25 into phosgene, hydrogen chloride and optionally inert gas or solvent vapor, and to pass the phosgene and optionally solvent, for example, back into the process. The hydrogen chloride can be diverted via chlorine synthesis for phosgene production, or alternatively also used for hydrochloric acid production or vinyl chloride production.

Since the amine is supplied to the centrifugal reactor 1 in liquid form and is not vaporized, the process according to the invention is especially suitable for performance of the amine phosgenation to prepare isocyanates for amines which cannot be vaporized and which have a very high vaporization temperature. The process according to the invention is particularly suitable for phosgenation of MDA or polymeric MDA to prepare the corresponding isocyanates or polyisocyanates in each case.

LIST OF REFERENCE NUMERALS 1 centrifugal reactor
3 first feed
5 second feed
7 central axis
9 rotating packing
11 shaft
13 housing
15 motor
17 outer periphery
19 outlet
21 gas outlet
23 gas inlet
25 offgas

The invention claimed is:

1. A process for preparing an isocyanate, a polyisocyanate, or both an isocyanate and a polyisocyanate by reacting a corresponding amine with phosgene, optionally in the presence of an inert medium, in a reactor, a first reactant stream comprising the amine being supplied to the reactor in liquid form, and a second reactant stream comprising the phosgene being supplied to the reactor in gaseous form, wherein the reactor is a centrifugal reactor having a packing which rotates about a central axis in a housing, the first reactant stream and the second reactant stream being supplied to the rotating packing such that the reactant streams are mixed due to the centrifugal force in the rotating packing and are transported outward, the mixing in the rotating packing resulting in reaction of the phosgene with the amine to give the corresponding isocyanate, polyisocyanate or both isocyanate and polyisocyanate.

2. The process according to claim 1, wherein the phosgene is added in excess.

3. The process according to claim 1, wherein the reaction is performed at a pressure in the range from 1 to 20 bar.

4. The process according to claim 1, wherein the reaction is performed at a temperature in the range from 50 to 400° C.

5. The process according to claim 1, wherein the centrifugal reactor is operated in such a way that a centrifugal acceleration of 1 to 5000 g acts within the contact region of packing and liquid phase, where g is the acceleration due to gravity.

6. The process according to claim 1, wherein the first reactant stream is supplied centrally to the rotating packing via a first feed, and the second reactant stream to the rotating packing via a second feed.

7. The process according to claim 1, wherein the rotating packing is porous and has a specific surface area of more than 200 m$^2$/m$^3$.

8. The process according to claim 1, wherein the rotating packing is manufactured from a metal or a ceramic.

9. The process according to claim 1, wherein the rotating packing is formed from unordered fibers, a bed of random packing or a bed of spheres, or is in the form of a foam or of structured internals.

10. The process according to claim 1, wherein the rotating packing is surrounded by a ring which deflects the reaction mixture flowing through the rotating packing to an outlet.

11. The process according to claim 1, wherein the reaction of the phosgene with the amine gives the corresponding isocyanate.

12. The process according to claim 1, wherein the reaction of the phosgene with the amine gives the corresponding polyisocyanate.

13. The process according to claim 1, wherein the reaction of the phosgene with the amine gives the corresponding isocyanate and polyisocyanate.

14. The process according to claim 1, wherein
the phosgene is added in excess;
the reaction is performed at a pressure in the range from 1 to 10 bar;
the reaction is performed at a temperature in the range from 100 to 300° C.; and
the centrifugal reactor is operated in such a way that a centrifugal acceleration of 10 to 1000 g acts within the contact region of packing and liquid phase, where g is the acceleration due to gravity.

15. The process according to claim 2, wherein the mole ratio of phosgene to amine groups is 1.1:1 to 4:1.

16. The process according to claim 14, wherein the mole ratio of phosgene to amine groups is 1.1:1 to 4:1.

17. The process according to claim 16, wherein:
the first reactant stream is supplied centrally to the rotating packing via a first feed, and the second reactant stream to the rotating packing via a second feed; and
the rotating packing is porous and has a specific surface area of more than 200 m$^2$/m$^3$.

18. The process according to claim 17, wherein the rotating packing is manufactured from a metal or a ceramic.

19. The process according to claim 17, wherein the rotating packing is formed from unordered fibers, a bed of random packing or a bed of spheres, or is in the form of a foam or of structured internals.

20. The process according to claim 17, wherein the rotating packing is surrounded by a ring which deflects the reaction mixture flowing through the rotating packing to an outlet.

* * * * *